United States Patent
Breton et al.

(12)

(10) Patent No.: US 6,753,000 B2
(45) Date of Patent: Jun. 22, 2004

(54) HYDROXYSTILBENE/ASCORBIC ACID COMPOSITIONS FOR TREATING SKIN AFFLICTIONS

(75) Inventors: Lionel Breton, Versailles (FR); Christel Liviero, Paris (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 10/222,913

(22) Filed: Aug. 19, 2002

(65) Prior Publication Data

US 2003/0031693 A1 Feb. 13, 2003

Related U.S. Application Data

(62) Division of application No. 09/607,926, filed on Jun. 30, 2000, now Pat. No. 6,440,433.

(30) Foreign Application Priority Data

Jul. 2, 1999 (FR) .............................................. 99 08570

(51) Int. Cl.[7] .......................... A61K 7/00; A61K 7/035; A61K 31/205; A61K 31/065; A61K 31/05
(52) U.S. Cl. ......................... 424/401; 424/69; 514/556; 514/726; 514/733
(58) Field of Search ................... 424/401, 69; 514/556, 514/726, 733

(56) References Cited

U.S. PATENT DOCUMENTS

| 4,784,847 | A | | 11/1988 | Zulliger-Bopp et al. |
|---|---|---|---|---|
| 5,747,536 | A | | 5/1998 | Cavazza |
| 5,804,594 | A | * | 9/1998 | Murad ......................... 514/474 |
| 6,124,348 | A | * | 9/2000 | Wells et al. ................. 514/474 |
| 6,124,364 | A | | 9/2000 | Breton et al. |
| 6,147,121 | A | | 11/2000 | Breton et al. |
| 6,270,780 | B1 | * | 8/2001 | Carson et al. .............. 424/401 |

FOREIGN PATENT DOCUMENTS

| EP | 0 773 020 A2 | | 5/1997 |
|---|---|---|---|
| GB | 2 317 561 A | | 4/1998 |
| JP | A-8-175960 | | 7/1996 |
| WO | WO 99/04747 | * | 2/1999 |

OTHER PUBLICATIONS

STN, Serveur de bases de Donnees, Karlsruhe, DE, Fichier CAPLUS, AN=1996:548009 XP002136068 & JP 08 175960 A(KAO Corp); publication date=1996.

STN, Serveur de Bases de Bonnees, Kaarlsruhe, DE, Fichier CAPLUS, AN=1997:387289 XP002136069; publication date=1997.

* cited by examiner

*Primary Examiner*—Shenglun Wang
(74) *Attorney, Agent, or Firm*—Burns, Doane, Swecker & Mathis, L.L.P.

(57) ABSTRACT

Cosmetic/dermatological compositions, well suited, e.g., for skin-firming and anti-aging applications, as well as for stimulating the proliferation of dermal fibroblasts, comprise effective skin affliction-alleviating amounts of (a) at least one hydroxystilbene compound, in immixture with (b) at least one ascorbic acid compound, advantageously formulated into a topically applicable, physiologically/ cosmetically acceptable vehicle, diluent or carrier therefor.

12 Claims, No Drawings

US 6,753,000 B2

HYDROXYSTILBENE/ASCORBIC ACID COMPOSITIONS FOR TREATING SKIN AFFLICTIONS

CROSS-REFERENCE TO PRIORITY APPLICATION

This application is a divisional application of 09/607,926, filed Jun. 30, 2000, claims priority under 35 U.S.C. §119 of FR-99/08570, filed Jul. 2, 1999, hereby expressly incorporated by reference.

BACKGROUND OF THE INVENTION

1. Technical Field of the Invention

The present invention relates to novel cosmetic/dermatological compositions comprising at least one hydroxystilbene in intimate admixture with ascorbic acid, especially for skin-firming applications.

In particular, the novel compositions of this invention are well suited to stimulate the restructuring of the skin and/or mucous membranes by stimulating the proliferation of the dermal fibroblasts.

2. Description of the Prior Art

Human skin includes two compartments or constituents, i.e., a superficial compartment, the epidermis, and a deep compartment, the dermis.

Natural human skin is principally composed of three types of cell: the keratinocytes, which are the vast majority, the melanocytes and the Langerhans cells. Each of these cell types contributes, by virtue of its intrinsic functions, towards the essential role played in the body by the skin.

The dermis provides the epidermis with a soft support. It is also the epidermis' nourishing factor. It primarily includes fibroblasts and an extracellular matrix itself composed of different extracellular proteins, among which are, in particular, collagen, elastin and various glycoproteins. This assembly of extracellular components is synthesized by the fibroblasts. Leukocytes, mastocytes and tissue macrophages are also found in the dermis. Too, the dermis contains blood vessels and nerve fibers.

On account of their activity in the synthesis of the extracellular matrix proteins (proteoglycans, collagen fibers and other structural glycoproteins), the fibroblasts are the principal factors involved in the structural development of the dermis.

The collagen fibers provide the dermis with solidity. They are very strong, but are sensitive to certain enzymes generally referred to as collagenases. In the dermis, the collagen fibers comprise fibrils sealed together, thus forming more than ten different types of structure. The structure of the dermis is essentially due to the overlapping of the trapped collagen fibers. The collagen fibers contribute to the skin's tonicity. The collagen fibers are regularly renewed, but this renewal decreases with age, thus leading, especially, to a thinning of the dermis. This thinning of the dermis is also due to pathological causes such as, for example, the hypersecretion of corticoid hormones, certain diseases (Marfan's syndrome, Ehlers-Danlos syndrome) or vitamin deficiencies (scurvy). It is also accepted that extrinsic factors such as ultraviolet radiation, tobacco or certain treatments (retinoic acid and derivatives, glucocorticoids, vitamin D and derivatives, for example) also have an effect on the skin and on its collagen level.

Degradation of the collagen fibers results, notably, in the appearance of loose, wrinkled skin which individuals have always tried to combat, since skin which looks smooth and taut is obviously more preferred.

Moreover, during menopause, the principal changes relating to the dermis are a decrease in the level of collagen and in the thickness of the dermis. In menopausal women, this results in thinning of the skin. Women thus experience a sensation of "dry skin" or of skin which feels tight, and an increase in the level of surface wrinkles and fine lines developed. The skin feels rough to the touch. Lastly, the skin is less supple. It is demonstrated that women gradually lose their level of collagen yearly after menopause and that 30% of the overall level is lost in the first five years after menopause.

Thus, serious need continues to exist for alternative active agents that maintain the level of collagen in the skin and also maintain the smooth and taut appearance of the skin.

One approach for achieving this result entails stimulating the proliferation of the fibroblasts and, consequently, on account of the increase in the number of secretory cells in the dermis, also maintaining or even reinforcing/enhancing the synthesis of collagen.

SUMMARY OF THE INVENTION

It has now surprisingly and unexpectedly been determined that association of at least one hydroxystilbene with ascorbic acid or one of the analogs thereof presents the attribute of stimulating the proliferation of the dermal fibroblasts in proportions that are higher than those which would reasonably be expected by simple addition of the effects of each of these components taken separately.

DETAILED DESCRIPTION OF BEST MODE AND SPECIFIC/PREFERRED EMBODIMENTS OF THE INVENTION

More particularly according to the present invention, the subject hydroxystilbenes are compounds having the following structural formula (I):

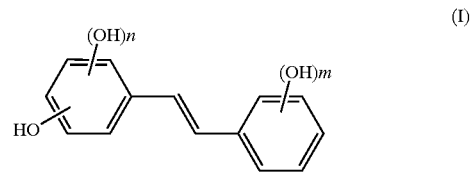

in which n is an integer ranging from 0 to 4, inclusive, and m is an integer ranging from 0 to 5, inclusive.

These compounds can be in cis- or trans-configuration.

According to this invention, by the term "hydroxystilbene" are intended both the compounds of formula I and the hydroxyalkyl derivatives thereof.

The hydroxystilbenes are compounds that exist in the natural state in plants of the Spermatophyte class and particularly in vine. Such compounds as, for example, resveratrol are found in grapes and in wine.

In the prior art, the hydroxystilbenes are useful, inter alia, as depigmenting agents (JP-87192,040), as vasodilators (EP-96830,517), as antithrombin agents (JP-05016,413), for the treatment of various cardiovascular conditions (CA-2, 187,990), as mutagenesis and carcinogenesis inhibitors (JP-06/24,967) or are described as antioxidants.

Among these compounds, resveratrol (or 3,5,4'-trihydroxystilbene) is particularly interesting for the activities described above, notably because it is a natural compound which is found in the skin of grapeseeds and in wine. In this regard, the review by Soleas et al. (*Clinical Biochemistry*, Vol. 30, No. 2, pp. 91–113 (1997)) well summarizes the state of the art regarding this compound and hydroxystilbenes.

Moreover, ascorbic acid (or vitamin C) is known to stimulate collagen synthesis by preventing, as a co-factor, the self-inactivation of the lysine and proline hydroxylase enzymes and by increasing the synthesis of procollagen mRNAs. Ascorbic acid (or vitamin C) is also known to stimulate the synthesis of elastin in the skin. In this regard, compare U.S. Pat. Nos. 5,801,192 and 4,983,382 and EP-0, 717,983. See, also the article entitled "Pola to incorporate vitamin C in new cosmetics line for skin care" from the Japan Economic Journal of Jun. 5, 1984 (page 15). Thus, it has been described that ascorbic acid in cosmetic compositions is useful for treating wrinkles (*Fragrance Journal*, Vol. 8, No. 6(45) (1980) pp. 38–43, "Cosmetic and vitamin action and safety to dermatology").

Thus, the present invention features compositions comprising, in a physiologically acceptable medium, at least one hydroxystilbene in immixture with ascorbic acid or with an analog thereof.

The subject compositions are particularly suited for stimulating the proliferation of dermal fibroblasts.

Exemplary hydroxystilbenes according to this invention are mono-, di-, tri-, tetra-, penta-, hexa-, hepta-, octa- and nonahydroxystilbenes, or, alternatively, hydroxyalkyl derivatives thereof.

According to the invention, the hydroxystilbenes can be used alone or as mixtures of any nature and can be of natural or synthetic origin.

The hydroxystilbenes according to the invention are preferably selected from among:

4'-hydroxystilbene,
2',4'-dihydroxystilbene,
3',4'-dihydroxystilbene,
4,4'-dihydroxystilbene,
2',4',4-trihydroxystilbene,
3',4',4-trihydroxystilbene,
2,4,4'-trihydroxystilbene,
3,4,4'-trihydroxystilbene,
3,4',5-trihydroxystilbene,
2', 3,4-trihydroxystilbene,
2,3', 4-trihydroxystilbene,
2',2,4'-trihydroxystilbene,
2,4,4', 5-tetrahydroxystilbene,
2',3,4',5-tetrahydroxystilbene,
2,2', 4,4'-tetrahydroxystilbene,
3,3', 4',5-tetrahydroxystilbene,
2,3', 4,4'-tetrahydroxystilbene,
3,3',4,4'-tetrahydroxystilbene,
3,3',4',5,5'-pentahydroxystilbene,
2,2', 4,4',6-pentahydroxystilbene,
2,3', 4,4',6-pentahydroxystilbene,
2,2', 4,4',6,6'-hexahydroxystilbene.

3,4',5-Trihydroxystilbene, or resveratrol, is the preferred compound according to the invention.

The ascorbic acid analogs are more particularly the salts thereof, especially sodium ascorbate, magnesium or sodium ascorbyl phosphate, the esters thereof, especially the acetic, propionic, palmitic, cinnamic or ferulic esters thereof, or the sugars thereof, especially glycosylated ascorbic acid. Thus, by the term "ascorbic acid compound" are intended ascorbic acid itself, as well as the analogs thereof The ascorbic acid is typically in L-configuration, since it is usually extracted from natural products.

According to the invention, the ascorbic acid and/or the analogs thereof can be used alone or as mixtures of any nature and can be of natural or synthetic origin.

The compositions of the invention are particularly useful for topical application onto the skin and/or mucous membranes.

As indicated above, collagen is involved in the solidity of the dermis, and thus in the firmness of the skin and/or mucous membranes. Also, the fibroblasts are responsible for the synthesis of the proteins of the extracellular dermal matrix, in particular of collagen.

Thus, the present invention features compositions comprising at least one hydroxystilbene in admixture with ascorbic acid, such compositions being well suited to preventively or curatively treat the signs of aging of the skin, more particularly to preventively or curatively treat or combat loose and/or wrinkled skin.

The subject compositions are especially well suited to reduce the signs of aging of the skin, more particularly to reduce the appearance of loose and/or wrinkled skin.

The present invention also features compositions comprising at least one hydroxystilbene in combination with ascorbic acid or analog thereof, for stimulating firming of the skin.

Too, this invention features compositions comprising at least one hydroxystilbene in combination with ascorbic acid or an analog thereof, for promoting the smoothness of the skin and/or to make the skin taut.

In another embodiment of the invention, compositions comprising at least one hydroxystilbene in combination with ascorbic acid or an analog thereof are used to combat the effects of menopause on the skin, more particularly the effects of menopause on collagen and/or fibroblasts.

The amounts of hydroxystilbene and of ascorbic acid or analogs thereof which are administered according to the invention obviously depend on the desired effect.

For example, the amount by weight of hydroxystilbene which can be administered according to the invention advantageously ranges, for example, from 0.001% to 10% and preferably from 0.005% to 5% relative to the total weight of the composition.

To provide an order of magnitude, the amount by weight of ascorbic acid or of analogs thereof which is administered according to the invention advantageously represents from 0.001% to 20% relative to the total weight of the composition, preferably from 0.1% to 15% relative to the total weight of the composition and, more advantageously, from 3% to 10% relative to the total weight of the composition.

In the compositions of the invention, the weight ratio between the hydroxystilbene and the ascorbic acid advantageously ranges from $5 \cdot 10^{-5}$ to $10^{+4}$ and preferably from $10^{-3}$ to 2.

In addition, the compositions of the invention are administered for a period of time which is sufficient to elicit the expected results. To provide an order of magnitude, this period of time can be a minimum of 3 weeks, but can also be more than 4 weeks, or even more than 8 weeks.

The subject compositions are preferably intended for cosmetic or dermatological usage, advantageously cosmetic use.

The compositions of the invention for topical application contain a physiologically acceptable medium, i.e., a medium which is compatible with the skin, including the scalp, mucous membranes and/or the eyes, and can especially constitute a cosmetic or dermatological composition.

The present invention the combination of at least one hydroxystilbene and of ascorbic acid or an analog thereof, to preventively or curatively treat the signs of aging of the skin, more particularly to preventively or curatively treat loose and/or wrinkled skin.

The subject compositions are preferably well suited to reduce the signs of aging of the skin, more particularly to reduce the appearance of loose and/or wrinkled skin.

This invention also features the combination of at least one hydroxystilbene and ascorbic acid or analog thereof for skin-firming applications.

Thus, this invention features the combination of at least one hydroxystilbene and of ascorbic acid or an analog thereof for smoothing the skin or making it taut.

Too, the present invention features compositions comprising at least one hydroxystilbene and ascorbic acid or analog thereof to stimulate the proliferation of dermal fibroblasts.

Lastly, the present invention features compositions comprising at least one hydroxystilbene and ascorbic acid or analog thereof, to combat the effects of menopause on the skin, more particularly the effects of menopause on the fibroblasts.

It will be appreciated that the compositions according to the invention comprise a cosmetically acceptable support (vehicle, diluent or carrier) i.e., a support which is compatible with the skin, mucous membranes, the nails and the hair, and can be in any pharmaceutical form normally used for topical application, in particular in the form of an aqueous, aqueous/alcoholic or oily solution, an oil-in-water or water-in-oil or multiple emulsion, an aqueous or oily gel, a liquid, pasty or solid anhydrous product, a dispersion of oil in an aqueous phase with the aid of spherules, it being possible for these spherules to be polymer nanoparticles such as nanospheres and nanocapsules or more preferably lipid vesicles of ionic and/or nonionic type.

The subject compositions can be more or less fluid and can be formulated as a white or colored cream, an ointment, a milk, a lotion, a serum, a gel, a paste or a mousse. They can optionally be applied to the skin in the form of an aerosol. They can also be in solid form, and, for example, be in the form of a tube or stick. They can be used as a care product, as a cleansing product, as a makeup product or as a simple deodorant product.

In known fashion, the compositions according to the invention can also contain adjuvants and additives that are common in cosmetics and dermatology, such as hydrophilic or lipophilic gelling agents, hydrophilic or lipophilic active agents, preservatives, antioxidants, solvents, fragrances, fillers, screening agents, pigments, chelating agents, odor absorbers, dyestuffs and colorants. The amounts of these various adjuvants and additives are those used conventionally in the fields under consideration, and, for example, constitute from 0.01% to 20% relative to the total weight of the composition. Depending on their nature, these adjuvants and additives can be formulated into the fatty phase, into the aqueous phase, into the lipid vesicles and/or into the nanoparticles.

When a composition of the invention is an emulsion, the proportion of the fatty phase advantageously ranges from 5% to 80% by weight, and preferably from 5% to 50%, relative to the total weight of the composition. The oils, the emulsifiers and the co-emulsifiers formulated into the composition in emulsion form are selected from among those conventional in the fields under consideration. The emulsifier and the co-emulsifier are typically present in the compositions in a proportion ranging from 0.3% to 30% by weight, and preferably from 0.5% to 20%, relative to the total weight of the composition.

Exemplary oils which can be formulated into the composition of the invention, include mineral oils, oils of plant origin (apricot oil, sunflower oil), oils of animal origin, synthetic oils, silicone oils and fluoro oils (perfluoropolyethers). Fatty alcohols (cetyl alcohol), fatty acids and waxes (beeswax) can also be used as fatty substances.

Exemplary emulsifiers and co-emulsifiers include, for example, fatty acid esters of polyethylene glycol, such as PEG-40 stearate and PEG-100 stearate, and fatty acid esters of polyols, such as glyceryl stearate and sorbitan tristearate.

And exemplary hydrophilic gelling agents include in particular, carboxyvinyl polymers (carbomer), acrylic copolymers such as acrylatealkylacrylate copolymers, polyacrylamides, polysaccharides, natural gums and clays, and exemplary lipophilic gelling agents include the modified clays such as bentones, metal salts of fatty acids, hydrophobic silica and polyethylenes.

The subject compositions can contain other hydrophilic active agents such as proteins or protein hydrolysates, amino acids, polyols, urea, allantoin, sugars and sugar derivatives, water-soluble vitamins, plant extracts and hydroxy acids.

Retinol (vitamin A) and derivatives thereof, tocopherol (vitamin E) and derivatives thereof, essential fatty acids, ceramides, essential oils and salicylic acid and derivatives thereof are representative lipophilic active agents.

According to the invention, in combination with the hydroxystilbene can be associated compounds selected from among:

(1) plant hormones;

(2) calcium antagonists such as verapamil and diltiazem;

(3) OH radical scavengers such as dimethyl sulfoxide;

(4) chlorine-channel openers (5) plant extracts such as those from Iridaceae, from Rosaceae or from soybean, these extracts also possibly containing isoflavones;

(6) extracts from microorganisms including, in particular, bacterial extracts such as those from non-photosynthetic filamentous bacteria.

Other compounds are also intended, namely, for example, potassium-channel openers such as diazoxide and minoxidil, spiroxazone, phospholipids such as lecithin, linoleic and linolenic acids, salicylic acid and derivatives thereof described in FR-2,581,542, such as salicylic acid derivatives bearing an alkyl group containing from 2 to 12 carbon atoms in position 5 of the benzene ring, hydroxycarboxylic or ketocarboxylic acids and their esters, lactones and their corresponding salts, anthralin, carotenoids, eicosatetraenoic and eicosatrienoic acids or the esters and amides thereof, and vitamin D and derivatives thereof.

According to the invention, it is also intended, inter alia, to combine the at least one hydroxystilbene with other active agents suited, in particular, for preventing and/or treating a variety of skin conditions. Exemplary such active agents include:

(a) agents which modify skin differentiation and/or proliferation and/or pigmentation, such as retinoic acid and its isomers, retinol and its esters, vitamin D and derivatives thereof, estrogens such as estradiol, kojic acid or hydroquinone;

(b) antibacterial agents such as clindamycin phosphate, erythromycin or antibiotics of the tetracycline class;

(c) agents which modify the adhesion of bacteria to the skin and/or to mucous membranes, such as honey, in particular acacia honey and certain sugar derivatives;

(d) antiparasitic agents, in particular metronidazole, crotamiton or pyrethroids;

(e) antifungal agents, in particular compounds of the imidazole class such as econazole, ketoconazole or miconazole or their salts, polyene compounds such as amphotericin B, compounds of the allylamine family such as terbinafine, or octopirox;

(f) antiviral agents such as acyclovir;

(g) steroidal anti-inflammatory agents such as hydrocortisone, betamethasone valerate or clobetasol propionate, or nonsteroidal anti-inflammatory agents such as ibuprofen and its salts, diclofenac and its salts, acetylsalicylic acid, acetaminophen or glycyrrhetinic acid;

(h) anaesthetics such as lidocaine hydrochloride and derivatives thereof;

(i) anti-pruriginous agents such as thenaldine, trimeprazine or cyproheptadine;

(j) keratolytic agents such as α- and β-hydroxycarboxylic or β-ketocarboxylic acids, their salts, amides or esters, and more particularly hydroxy acids such as glycolic acid, lactic acid, salicylic acid, citric acid and fruit acids in general, and 5-n-octanoylsalicylic acid;

(k) anti-free-radical agents such as α-tocopherol or its esters, superoxide dimutases, certain metal-chelating agents or ascorbic acid and its esters;

(l) anti-seborrhoeic agents such as progesterone;

(m) antidandruff agents such as octopirox or zinc pyrithione;

(n) anti-acne agents such as retinoic acid or benzoyl peroxide;

(o) substances such as antagonists of substance P, of CGRP or of bradykinin or NO synthase inhibitors or alternatively sodium-channel inhibitors, compounds described as being active in the treatment of sensitive skin and as having anti-irritant effects, in particular with respect to irritant compounds which may be present in the compositions.

Moisturizers such as polyols (for example glycerol), vitamins (for example D-panthenol), anti-inflammatory agents, calmatives (allantoin, cornflower water), UVA and UVB screening agents, matt-effect agents (for example the partially crosslinked polydimethylorganosiloxanes marketed under the trademark KSG® by Shin Etsu), and mixtures thereof are particularly useful active agents.

Anti-wrinkle active agents, and in particular tautening products such as plant proteins and their hydrolysates, in particular the soybean protein extract marketed under the trademark Eleseryl® by LSN or the oat derivative marketed under the trademark Reductine® by Silab, can also be added.

Since the skin comprises many more components or constituents than just collagen and fibroblasts, it is found to be advantageous, when a combination of hydroxystilbene and ascorbic acid is used according to the invention, to simultaneously promote the synthesis of these other components, for example such as the lipids, and/or to promote the proliferation of other cell components, for example the keratinocytes.

Thus, this invention features cosmetic compositions comprising, in a cosmetically acceptable medium, a combination of at least one hydroxystilbene and of ascorbic acid or an analog thereof and at least one other active species for stimulating the synthesis of lipids and/or the proliferation of keratinocytes.

In this regard, active species for stimulating the synthesis of lipids which are exemplary are plant hormones, such as auxins, or compounds of plant origin, such as cinnamic acid, and products for stimulating the proliferation of keratinocytes which are exemplary are compounds of plant origin, such as phloroglucinol.

Thus, in addition to hydroxystilbene and ascorbic acid, the compositions according to the invention can comprise cinnamic acid or derivatives thereof and/or a plant hormone, particularly an auxin selected from among indoleacetic acid (IAA), 4-chloroindole-3-acetic acid (4-Cl-IAA), phenylacetic acid (PAA), indole-3-butyric acid (IBA), 2,4-dichlorophenoxyacetic acid (2,4-D), α-naphthaleneacetic acid (α-NAA), β-naphthoxyacetic acid, indolethanol, indoleacetaldehyde and indoleacetonitrile and/or a plant compound such as phloroglucinol.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Study of the Effect of Resveratrol on the Proliferation of Dermal Fibroblasts

The study has carried out by measuring the incorporation of radioactive thymidine into normal human dermal fibroblast cultures.

The fibroblast cultures were prepared according to the standard methods of cell culturing, i.e., in MEM/M199 medium marketed by Gibco, in the presence of sodium bicarbonate (1.87 mg/ml), L-glutamine (2 mM), penicillin (50 IU/ml) and 10% foetal calf serum (Gibco).

The test was carried out on cell cultures at 80% of confluence on 24-well plates. Resveratrol, at a concentration of 1.25 $\mu$M and 5 $\mu$M, was placed in contact with the cells for 48 hours. Labeling with tritiated thymidine ([methyl-3H] thymidine marketed by Amersham, 82 Ci/mmol) was carried out for 24 hours.

The level of tritiated thymidine incorporated was measured at the end of the test by acidic precipitation of the proteins on filters and counting by liquid scintillation.

The results were evaluated relative to a control consisting of cells which had not been treated.

A positive control [EGF: Epidermal Growth Factor] at $1.67 \times 10^{-3}$ $\mu$M, which was known to stimulate fibroblast proliferation, was introduced into the test by way of reference.

The results of this test are reported in the Table below:

TABLE

| Treatment | cpm | s.d. | % | p |
|---|---|---|---|---|
| Untreated | 10320 | 1427 | 100 | — |
| EGF (1.67 × 10$^{-3}$ $\mu$M) | 29214 (+18894) | 1825 | 283 (+183) | <0.001 |
| 20 $\mu$m vitamin C | 13595 (+3275) | 1394 | 132 (+32) | <0.05 |
| 5.00 $\mu$M resveratrol | 11365 (+1045) | 613 | 110 (+10) | >0.05 |
| 5 $\mu$M resveratrol + 20 $\mu$M vitamin C | 18944 (+8624) | 331 | 184 (+84) | <0.001 |

( . . . ): difference relative to the untreated control
cpm: counts per minute
s.d.: standard deviation
p: confidence interval calculated according to the Dunett method.

The results reported in the table above unambiguously evidence that the resveratrol/vitamin C combination synergistically stimulated fibroblast proliferation markedly more than would have been predicted by adding the effects measured for resveratrol and vitamin C used individually. A synergistic effect between resveratrol and vitamin C on fibroblast proliferation exists when the two products are used simultaneously.

EXAMPLE 2

The following are specific examples of formulations according to the invention.

These compositions were formulated according to typical cosmetic/pharmacy techniques.

| Composition 1: Care cream | | |
|---|---|---|
| beeswax | | 1.50% |
| apricot kernel oil | | 13.00% |
| fragrance | | 0.40% |
| resveratrol | | 1.00% |
| ascorbic acid | | 5.00% |
| xanthan | | 0.50% |
| cyclopentadimethylsiloxane | | 5.00% |
| sucrose mono-di-palmitostearate | | 3.00% |
| methylglucose sesquistearate | | 3.00% |
| stearic acid | | 1.00% |
| cetyl alcohol | | 3.00% |
| preservatives | | 0.30% |
| sterilized demineralized water | qs | 100.00% |

| Composition 2: Body oil | |
|---|---|
| liquid petroleum jelly | 47.99% |
| apricot kernel oil | 6.00% |
| fragrance | 1.00% |
| resveratrol | 0.50% |
| ascorbic acid | 3.00% |
| cyclopentadimethylsiloxane | 45.00% |

| Composition 3: Makeup-removing milk | |
|---|---|
| 2-ethylhexyl palmitate | 10.50% |
| liquid fraction of karite butter | 16.50% |
| preservatives | 0.30% |
| fragrance | 0.15% |
| resveratrol | 0.50% |
| ascorbic acid | 2.00% |
| sodium hydroxide | 0.04% |
| carboxyvinyl polymer | 0.20% |
| sterilized demineralized water | 69.80% |
| mixture of cetylstearyl glucoside and of cetyl and stearyl alcohols | 2.50% |

| Composition 4: Hair cream | |
|---|---|
| beeswax | 1.50% |
| apricot kernel oil | 13.00% |
| preservatives | 0.30% |
| fragrance | 0.40% |
| triethanolamine | 0.17% |
| resveratrol | 1.00% |
| ascorbic acid | 5.00% |
| beta-naphthoxyacetic acid | 0.01% |
| 2,4-dichlorophenoxyacetic acid | 0.01% |
| xanthan | 0.50% |

-continued

| Composition 4: Hair cream | | |
|---|---|---|
| cyclopentadimethylsiloxane | | 5.00% |
| sucrose mono-di-palmitostearate | | 3.00% |
| methylglucose sesquistearate | | 3.00% |
| stearic acid | | 1.00% |
| cetyl alcohol | | 3.00% |
| sterilized demineralized water | qs | 100.00% |

While the invention has been described in terms of various specific and/or preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method of stimulating the proliferation of dermal fibroblasts, the method comprising administering to an individual subject in need of such stimulation, a dermal fibroblast proliferation stimulating effective amount of a synergistic combination of resveratrol and vitamin C.

2. The method of claim 1, wherein the amount of resveratrol administered is between about 0.001% and about 5% by weight of a composition comprising the synergistic combination of resveratrol and vitamin C.

3. The method of claim 1, wherein the synergistic combination is administered in a composition comprising at least one agent selected from the group consisting of a hydrophilic gelling agent, a lipophilic gelling agent, a preservative, an additional antioxidant, a solvent, a fragrance, an additional vitamin, a filler, a UV-screening agent, a pigment, a chelating agent, an odor absorber, a dyestuff, a colorant, an oil, an emulsifier, a co-emulsifier, an antibacterial agent, an agent for combating parasites, an antifungal agent, an antiviral agent, an antiinflammatory agent, an antipruriginous agent, an anaesthetic agent, a keratolytic agent, an agent for combating free radicals, an agent for modifying the adhesion of bacteria to the skin and/or to mucous membranes, an antiseborrhoeic agent, an antidandruff agent, an antiacne agent, an agent which modulates cutaneous pigmentation and/or proliferation and/or differentiation, a substance P antagonist, a CGRP antagonist, a bradykinin antagonist, an NO-synthase inhibitor, a sodium-channel inhibitor, a moisturizer and an anti-wrinkle agent.

4. The method of claim 1, wherein the synergistic combination is administered in a composition formulated as a cream, an ointment, a milk, a lotion, a serum, a gel, a paste, a mousse, an aerosol, a cleansing product, a makeup product or a deodorant product.

5. A method of stimulating firming of the skin, the method comprising administering to an individual subject in need of such stimulation, a skin firming effective amount of a synergistic combination of resveratrol and vitamin C.

6. The method of claim 5, wherein the amount of resveratrol administered is between about 0.001% and about 5% by weight of a composition comprising the synergistic combination of resveratrol and vitamin C.

7. The method of claim 5, wherein the synergistic combination is administered in a composition comprising at least one agent selected from the group consisting of a hydrophilic gelling agent, a lipophilic gelling agent, a preservative, an additional antioxidant, a solvent, a fragrance, an additional vitamin, a filler, a UV-screening agent, a pigment, a chelating agent, an odor absorber, a dyestuff, a colorant, an oil, an emulsifier, a co-emulsifier, an antibacterial agent, an agent for combating parasites, an antifungal agent, an antiviral agent, an antiinflammatory agent, an antipruriginous agent, an anaesthetic agent, a keratolytic agent, an agent for combating free radicals, an agent for modifying the adhesion of bacteria to the skin and/or to mucous membranes, an antiseborrhoeic agent, an antidandruff agent, an antiacne agent, an agent which modulates cutaneous pigmentation and/or proliferation and/or differentiation, a substance P antagonist, a CGRP antagonist, a bradykinin antagonist and an NO-synthase inhibitor, a sodium-channel inhibitor, a moisturizer and an anti-wrinkle agent.

8. The method of claim 5, wherein the synergistic combination is administered in a composition formulated as a cream, an ointment, a milk, a lotion, a serum, a gel, a paste, a mousse, an aerosol, a cleansing product, a wakeup product or a deodorant product.

9. A method of stimulating tautening of the skin, the method comprising administering to an individual subject in need of such stimulation, a skin tautening effective amount of a synergistic combination of resveratrol and vitamin C.

10. The method of claim 9, wherein the amount of resveratrol administered is between about 0.001% and about 5% by weight of a composition comprising the synergistic combination of resveratrol and vitamin C.

11. The method of claim 9, wherein the synergistic combination is administered in a composition comprising at least one agent selected from the group consisting of a hydrophilic gelling agent, a lipophilic gelling agent, a preservative, an additional antioxidant, a solvent, a fragrance, an additional vitamin, a filler, a UV-screening agent, a pigment, a chelating agent, an odor absorber, a dyestuff, a colorant, an oil, an emulsifier, a co-emulsifier, an antibacterial agent, an agent for combating parasites, an antifungal agent, an antiviral agent, an antiinflammatory agent, an antipruriginous agent, an anaesthetic agent, a keratolytic agent, an agent for combating free radicals, an agent for modifying the adhesion of bacteria to the skin and/or to mucous membranes, an antiseborrhoeic agent, an antidandruff agent, an antiacne agent, an agent which modulates cutaneous pigmentation and/or proliferation and/or differentiation, a substance P antagonist, a CGRP antagonist, a bradykinin antagonist and an NO-synthase inhibitor, a sodium-channel inhibitor, a moisturizer and an anti-wrinkle agent.

12. The method of claim 9, wherein the synergistic combination is administered in a composition formulated as a cream, an ointment, a milk, a lotion, a serum, a gel, a paste, a mousse, an aerosol, a cleansing product, a makeup product or a deodorant product.

* * * * *